(12) United States Patent
Jaynes

(10) Patent No.: US 6,255,282 B1
(45) Date of Patent: *Jul. 3, 2001

(54) LYTIC PEPTIDES

(75) Inventor: Jesse M. Jaynes, Baton Rouge, LA (US)

(73) Assignee: Helix Biomedix, Inc., New Orleans, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/232,153

(22) Filed: Jan. 15, 1999

Related U.S. Application Data

(62) Division of application No. 08/301,736, filed on Sep. 6, 1994, now Pat. No. 5,861,478, which is a continuation of application No. 07/976,681, filed on Nov. 16, 1992, now abandoned, which is a continuation of application No. 07/846,771, filed on Mar. 6, 1992, now abandoned, which is a continuation of application No. 07/336,181, filed on Apr. 10, 1989, now abandoned, which is a continuation-in-part of application No. 07/102,175, filed on Sep. 29, 1987, now abandoned, which is a continuation-in-part of application No. 07/069,653, filed on Jul. 6, 1987, now abandoned.

(51) Int. Cl.$^7$ ............................ A61K 38/10; A61K 38/16

(52) U.S. Cl. ............................... 514/12; 514/12; 514/13; 514/2; 514/8; 514/14; 530/324; 530/310; 530/326; 435/259; 435/69.7; 435/252.3; 435/91.41

(58) Field of Search ............................... 435/259; 514/12, 514/13; 530/324, 326

(56) References Cited

U.S. PATENT DOCUMENTS

| | | | |
|---|---|---|---|
| 4,355,104 | 10/1982 | Hultmark et al. | 435/70 |
| 4,520,016 | 5/1985 | Hultmark et al. | 514/12 |
| 4,579,821 | 4/1986 | Palmiter et al. | 435/172.3 |
| 4,643,988 | 2/1987 | Segrest et al. | 514/12 |
| 4,704,362 | 11/1987 | Itakura et al. | 435/253 |
| 5,045,531 | 9/1991 | Berkowitz | 514/12 |
| 5,206,154 | 4/1993 | Lai | 435/697 |
| 5,208,220 | 5/1993 | Berkowitz | 514/13 |
| 5,357,044 | * 10/1994 | Lai et al. | 530/350 |
| 5,597,945 | 1/1997 | Jaynes et al. | 800/705 |
| 5,597,946 | * 1/1997 | Jaynes et al. | 800/205 |
| 5,962,410 | * 10/1999 | Jaynes et al. | 514/12 |

FOREIGN PATENT DOCUMENTS

| | | |
|---|---|---|
| 0157351 | 10/1985 | (DE) . |
| 0182278 | 5/1986 | (DE) . |
| PCTWO89/00199 | 1/1989 | (EP) . |
| 063949 | 11/1982 | (GB) . |
| 145338 | 6/1985 | (GB) . |
| 0184288 | 6/1986 | (GB) . |
| PCTWO86/04356 | 7/1986 | (WO) . |

OTHER PUBLICATIONS

Anderson, Lucy, *J. Cell Sci.*, Protein Synthesis and Uptake by Isolated Cecropia Oocytes, 1971, 8:735–750.

Andreu, D., *Proc. Natl. Acad. Sci.*, "Solid–phase synthesis of Cecropin A and Related Peptides", 1983, 80:6475–6479.

Andreu, D., *Biochemistry*, "N–Terminal Analogues of Cecropin A: Synthesis, Antibacterial Activity, and Conformation Properties", 1985, 24:1683–1688.

Bernheimer, A.W., *Biochimica et Biophysica Acta*, "Interactions between Membranes and Cytolytic Peptides", 1986, 864:123–141.

Bessler, W.G., *Biochemical and Biophysical Research Communications*, "Interaction of Membrane Modifying Peptide Antibiotics from *Trichoderma viride* with Leukocytes", 1979, 87:99–105.

Blasi, Udo, *Gen. Virol.*, "Influence of C–terminal Modifications of ΦX174 Lysis Gene E on its Lysis–inducing Properties", 1985, 66:1209–1213.

Boller, Thomas, *ULCA Symp. Mol. Cell. Biol.*, Newser, "Induction of Hydrolases as a Defense Reaction Against Pathogens", 1985 (Cell. Mol. Biol. Plant Stress).

Boman, H.G., *Developmental and Comparative Immunology*, "On the Primary Structures of Lysozyme, Cecropins and Attacins from *Hyalophora cecropia*", 1985, 9:551–558.

Boman, H.G., *Ann. Rev. Microbiol.*, "Cell–Free Immunity in Insects", 1987, 41:103–26.

Brillinger, G.U., *Arch. Microbiol.*, "Metabolic Products of Microoraganisms 181* . Chitin Synthase from Fungi, a Test Model for Substances with Insecticidal Properties", 1979, 121:71–74.

Buckley, K.J., *Mol. Gen. Genet.*, "Lytic Activity Localized to Membrane–spanning Region of ΦX174 E Protein", 1986, 204:120–125.

Chang et al., *Biochemistry*, 1983, 22:3250.

Chen, Hao–Chia, *FEBS Letters*, "Synthetic Magainin Analogues with Improved Antimicrobial Activity", 1988, 236:462–466.

Christensen, Bernd, *Proc. Natl. Acad. Sci.*, "Channel–forming Properties of Cecropins and Related Model Compounds Incorporated into Planar Lipid Membranes", 1988, 85:5072–5076.

(List continued on next page.)

Primary Examiner—Christopher S. F. Low
Assistant Examiner—Patricia Robinson
(74) Attorney, Agent, or Firm—Baker Botts L.L.P.

(57) ABSTRACT

Novel synthetic lytic and proliferative peptides were designed and constructed to encompass the structural features associated with lytic and proliferative activity. These compounds, along with the human β fibrin signal peptide share structural and functional properties of the known lytic peptides. These peptides are effective agents in the treatment of microbial infections including gram negative and gram positive bacteria, fungus, virus, yeast, and protozoa, in the lysis of cancer cells, and in the proliferation of fibroblasts and lymphocytes. Additional functions include synergy and use as general adjuvants and in the enhancement of wound healing.

24 Claims, 12 Drawing Sheets

OTHER PUBLICATIONS

Cuervo, Julio H., *Peptide Research*, "The Magainins: Sequence Factors Relevant to Increased Antimicrobial Activity and Decreased Hemolytic Activity", 1988, 1:81–86.

Deshpande, M.V., *Journal of Scientific and Industrial Research*, "Enzymatic Degradation of Chitin & Its Biological Applications", 1986, 45:273–281.

Drutz, David, *Basic & Clinical Immunology*, "Immunity & Infection", 1984, 197–203.

Eglitis, Martin A., *Science*, "Gene Expression in Mice After High Efficiency Retroviral–Mediated Gene Transfer", 1985, 230:1395–1398.

Engstrom, A., *The EMBO Journal*, "Insect Immunity. The Primary Structure of the Antibacterial Protein Attacin F and its Relations to Two Native Attacins from *Hyalophora cecropia*", 1984, 3:2065–2070.

Engstrom, A., *The EMBO Journal*, "Amino Acid and cDNA Sequences of Lysozyme from *Hyalophora cecropia*", 1985, 4:2119–2122.

Fingl, Edward, *The Pharmacological Basis of Therapeutics*, "General Principles", Chapter 1, 1975, p. 1–2.

Fuchs, R.L., *Applied and Environmental Microbiology*, "Cloning of a *Serratia marcescens* Gene Encoding Chitinase", 1986, 51:504–509.

Garcia, Lopez, *Biochem. Genetics*, "Production of Lysozyme of *Streptococcus pneumonia* in *Escherichia coli* by Recombinant DNA Technology", 1986, 106:190368d.

Garrett, Jinnie, *Mol. Gen. Genet.*, "Cell Lysis by Induction of Cloned Lambda Lysis Genes", 1981, 182:326–311.

Gelehrter, Thomas D., *Biochem. and Biophys. Res. Comm.*, Stimulation of Monovalent Ion Fluxes and DNA Synthesis in 3T3 Cells by Mellitin and Vasopressin is not Medeated by Phospholiped Deacylation, 1980, 97:716–724.

Goy, P., *Agro. Division Report*, "Spectrum of Activity of 1 Synthetic Cecropin: In Vitro and In Vivo Tests", 12 F Report 89013xx, Oct. 18, 1989.

Horwitz, Marc, *Mammalian Hormones*, "Genetic Improvement of Chitinase Production of *Serratia marcescens*", 1985, 102:21603R.

Hultmark, D., *Eur. J. Biochem.*, "Insect Immunity. Purification and Properties of Three Inducible Bactericidal Proteins from Hemolymph of Immunized Pupae of *Hyalophora cecropia*", 1980, 106:7–16.

Hultmark, D., *Eur. J. Biochem.*, "Insect Immunity: Isolation and Structure of Cecropin D Four Minor Antibacterial Components from Cecropia Pupae", 1982, 127:207–217.

Hultmark, D., *The EMBO Journal*, "Insect Immunity. Attacins, a Family of Antibacterial Proteins from *Hyalophora cecropia*", 1983, 2:571–576.

Huszar, D., *Proc. Natl. Acad. Sci. USA*, "Insertion of a Bacterial Gene the Mouse Germ Line Using an Infectious Retrovirus Vector", 1985, 82:8587–8591.

Jaynes, J.M., Departments of Biochemistry, Vet Science and Animal Science, L.S.U. "In Vitro Effect of Novel Lytic Peptides on *Plasmodium falciparum* and *Trypanosoma cruzi*" (date unknown).

Jaynes, J.M., *FASEB Journal*, "In Vitro Cytocidal Effect of Novel Lytic Peptides on *Plasmodium falciparum* and *Trypanosoma cruzi*", 1988, 2:2878–2883.

Jaynes, J.M., *Peptide Research*, "In Vitro Cytocidal Effect of Lytic Peptides on Several Transformed Mammalian Cell Lines", 1989.

Jaynes, J.M., *Drug News & Perspectives*, "Lytic Peptides Portend an Innovative Age in the Management and Treatment of Human Disease", 1990, 3:69–78.

Karser et al., *Science*, 1984, 223:249.

Kochum, K., *The EMBO Journal*, "Insect Immunity. Isolation and Sequence of Two cDNA Clones Corresponding to Acidic and Basic Attacins from *Hyalophora cecropia*", 1984, 3:2071–2075.

Lee, J.Y., *The EMBO Journal*, "Insect Immunity. Isolation of cDNA Clones Corresponding to Attacins and Immune Protein P4 from *Hysalphora cecropia*", 1983, 2:577–581.

Merrifield, R.B., *Biochemistry*, "Synthesis of the Antibacterial Peptide Cecropin A(1–33)", 1982, 21:5020–5031.

Nakai, T. *Chemical Abstracts*, "Synthesis of Self–defense Substance Produced by Silkworm, Lepidopteran, and Related Peptides", 1986, 106:214351w.

Nakajima, Yuki, *Biological Chemistry*, "Interaction Between Liposomes and Sarcotoxin IA, a Potent Antibacterial Protein of *Sarcophga peregrina* (Flex Fly)*", 1987, 262:1665–1669.

Natori, S., *Drugs of the Future*, "Future Drugs Mimicking Insect Defense proteins: Sarcophaga Lectic and Sarcotozin I", 1988, 13:59–68.

Okada, Masayuki, *Biochem. J.*, "Ionophre Activity of Sarcotoxin I, a Bactericidal Protein of *Sarcophaga peregrina*", 1985, 229:453–458.

Partial Search Report for European Patnet Application EP 88 90 6595, Jun. 27, 1991.

Partial Search Report for European Application No. EP 90 90 6453, Jun. 19, 1992.

Patent Cooperation Treaty International Search Report for International Application No. PCT/US88/02272, Nov. 15, 1988.

Patent Cooperation Treath International Search Report for International Application No. PCT/US90/01945, Jul. 30, 1990.

Rennell, et al., *Virology*, "Phage P22 Lysis Genes: Nucleotide Sequences and Functional Relationships with T4 and λ Genes", 1985, 143:280–289.

Shiba, T., *Chemical Abstracts*, "Antimicrobial Peptides from Silkworm Hemolymph", 1985, 104:230430k.

Skogen, William F., *Blood*, "Fibrinogen–Derived BB1–42 is a Multidomained Neutrophil Chemoattractant", 1988, 71:1475–1479.

Steiner, H., *Nature*, "Sequence and Specificity of two Antibacterial Proteins Involved in Insect Immunity", 1981, 292:246–248.

Supplementary Search Report for European Patent Application No. EP 88 90 6511, Jan. 18, 1991.

Van Hofsten, P., *Proc. Natl. Acad. Sci. USA*, "Molecular Cloning, cDNA Sequencing, and Chemical Synthesis of Cecropin B from *Hyalophora cecropia*", 1985, 82:2240–2243.

* cited by examiner

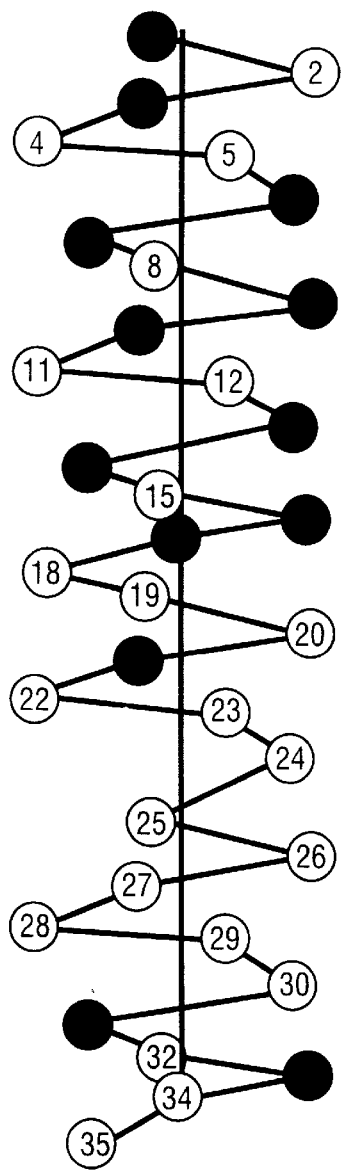
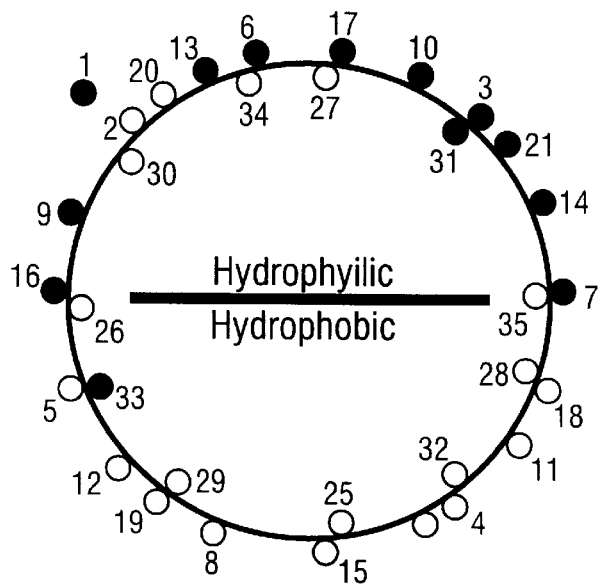
Natural Cecropin B Helical Wheel
FIG. 1B
FIG. 1A
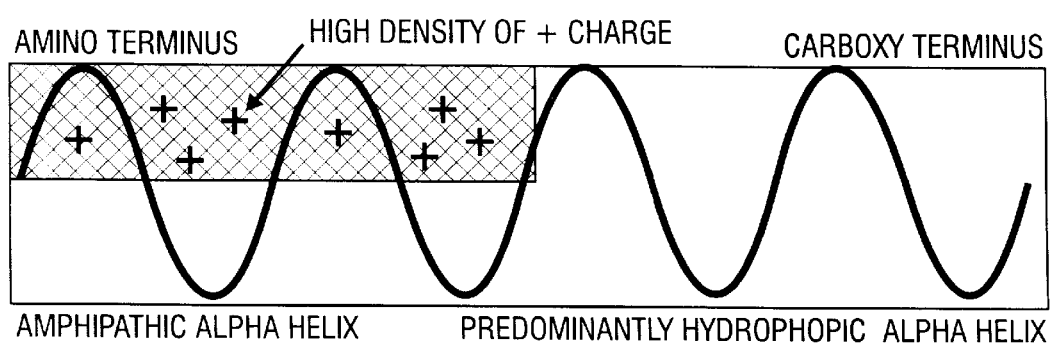
FIG. 1C Classes Of Lytic Peptide Analogs Classes Of Lytic Peptide Analogs

LYTIC PEPTIDE AMINO ACID SEQUENCES

| | Sequence | #A.A. |
|---|---|---|
| Cecropin B | .KWKVFKKIEKVGRNIRNGIVKAGPAIAVLGEAKAL | 35 |
| SB-37* | MP.KWKVFKKIEKVGRNIRNGIVKAGPAIAVLGEAKALG | 38 |
| LSB-37 | LP.KWKVFKKIEKVGRNIRNGIVKAGPAIAVLGEAKALG | 38 |
| SB-37 | MP.KEKVFLKIEKMGRNIRNGIVKAGPAIAVLGEAKALG | 38 |
| SHIVA-1 | MP.RWRLFRRIDRVGKQIKQGILRAGPAIALVGDARAVG | 38 |
| SHIVA-10 | .FAKKLAKKLKKLAKLALAL | 23 |
| SHIVA-11 | .FAKKLAKKLKKLAKLAKLALALKALALKAL | 31 |
| SHIVA-12 | .FAKKLAKKLKKLAKLAKLALALKALALKALALKALAL | 38 |
| β-FIBRIN SIGNAL | .MKRMVSWSFHKLLKTMKHLLLLLLCVFLVKS | 30 |
| MANITOU-1 | .MKRMVSWSFKKLKTMKKLLLLLLCVFLVKS | 30 |
| MANITOU-2 | .MKRMVSWSFRKLKTMKRLLLLLLCVFLVKS | 30 |
| HECATE-1 | .FALALKALKKALKKLKKALKKAL | 23 |
| HECATE-2 | .FAKLALAKLALAKLALKALKKLKKALKKAL | 31 |
| HECATE-3 | .FALAKLALAKLALALKALKKLKALKKLKKALKKAL | 38 |

FIG. 3A

| LYTIC PEPTIDE AMINO ACID SEQUENCES | #A.A. |
|---|---|
| ANUBIS-1 .FAKKLAKKLAKLAKKLAKKL | 23 |
| ANUBIS-2 .FAKKLAKKLKKLAKKLAKLAKKL | 23 |
| ANUBIS-3 .FAKKLAKKLKKLAKLAKKLAKKLKKLA | 31 |
| ANUBIS-4 .FAKKLAKKLKKLAKLAKKLAKKLKKLAKKLAKLAKLA | 38 |
| ANUBIS-5 .QAFQKLAKLAQQLAKKLQQLAKK | 23 |
| ANUBIS-8 .LKKLAKLAKKLAKLAKKLAKK | 21 |
| VISHNU-1 MP.KWKVFKKIEKVGRNIRN | 19 |
| VISHNU-2 MP.RWRLFRRIDRVGKQIKQ | 19 |
| VISHNU-3 MP.KEKVFLKIEKMGRNIRN | 19 |
| VISHNU-8 .MKRMVSWSFKKLKTMKKLL | 19 |

○ HYDROPHOBIC
● HYDROPHILIC
NOTE: 1 IS A CARBOXY TERMINUS

○ HYDROPHOBIC
● HYDROPHILIC
NOTE: 1 IS A CARBOXY TERMINUS

○ HYDROPHOBIC
● HYDROPHILIC
NOTE: 1 IS A CARBOXY TERMINUS

○ HYDROPHOBIC
● HYDROPHILIC
NOTE: 1 IS A CARBOXY TERMINUS

LEFT - Burned; infected; treated with cytolysin by injection.
RIGHT - Burned; not infected (control).

LEFT - Burned; infected; standard silver sulfadiazine treatment.
RIGHT - Burned; infected; treated topically with cytolysin.

LYTIC PEPTIDES

This is a divisional of application Ser. No. 08/301,736 filed Sep. 6, 1994 now U.S. Pat. No. 5,861,478, which is a continuation of Ser. No. 07/976,681 (now abandoned), filed Nov. 16, 1992, which is a continuation of Ser. No. 07/846, 771 (now abandoned), filed Mar. 6, 1992, which is a continuation of Ser. No. 07/336,181 (now abandoned), filed Apr. 10, 1989, which is a continuation-in-part of Ser. No. 07/102,175 (now abandoned), filed Sep. 29, 1987, which is a continuation-in-part of Ser. No. 07/069,653 (now abandoned), filed Jul. 6, 1987.

FIELD OF THE INVENTION

The present invention relates to novel lytic peptides, their use in methods for inhibiting eucaryotic pathogens, cancer cells and intracellularly infected cells, their use in methods for stimulating the proliferation of fibroblasts and lymphocytes, and in the process of wound healing. More particularly, this invention relates to the inhibition of such pathogens, cancers and infected cells, and the stimulation of fibroblasts and lymphocytes in mammals and other higher animals. The present invention also relates to the use of lytic peptides as general adjuvants.

BACKGROUND OF THE INVENTION

Many diseases of procaryotic origin, i.e. caused by pathogenic bacteria, are known. Such diseases are in general more easily treated than those of eucaryotic origin because of the marked differences between the invading procaryotes and the eucaryotic cells of the host. Thus, because of the differences between bacterial cells and those of the host, many antibiotics are known to specifically inhibit the invading bacteria without significant adverse effects on the host. In contrast, it has generally been more difficult to treat diseases of nonbacterial origin, such as malaria, sleeping sickness and Chagas' disease.

The property of certain peptides to induce lysis of procaryotic microorganisms such as bacteria are known. For example, U.S. Pat. Nos. 4,355,104 and 4,520,016 to Hultmark et al describe the bacteriolytic properties of some cecropins against Gram-negative bacteria. Quite interestingly, the cecropins described in the Hultmark et al. patents were not universally effective against all Gram-negative bacteria. For example, the cecropins described therein lysed *Serratia marcescens* D61108, but not *Serratia marcescens* D611. Moreover, cecropins have heretofore been reported to have no lytic activity towards eucaryotic cells such as insect cells, liver cells and sheep erythrocytes, as reported in the Hultmark patents; International Patent Publication WO/8604356; Andreu et al *Biochemistry,* vol. 24, pp. 1683–88 (1985); Boman et al, *Developmental and Comparative Immunology,* vol. 9, pp. 551–558 (1985); and Steiner et al., *Nature,* vol. 292, pp. 246–248 (1981).

Other lytic peptides heretofore known include, for example, the sarcotoxins and lepidopterans. Such peptides generally occur naturally in the immune system of *Sarcophaga peregrina* and the silkworm, lepidopteran, respectively, as reported in Nakajima et al, *The Journal of Biological Chemistry,* vol. 262, pp. 1665–1669 (1987) and Nakai et al, *Chem. Abst.* 106:214351w (1987).

The mechanism of action of the lytic peptides in the immune systems in which they occur is not entirely clear. There must, of course, be some aspect of the mechanism which regulates the specificity of the lytic peptides for invading pathogens among the cells of the host organism which must generally be preserved from lysis. For example, human complement fixation involves antibodies which are generally specific for certain antigens expressed by the invading pathogen. The activated components of complement attack the membrane of the invading cell to which they are bound by the antigen-antibody reaction to produce circular lesions which are probably formed as a result of insertion of the C9 protein into the membrane. The more primitive mechanisms involved in insect immunology are less specific, but the peptides involved apparently do not significantly lyse the host cells.

There are many differences between the membranes of different types of cells which can affect their susceptibility to lysis by the various lytic peptides. As suggested above, for example, some proteins are capable of lysing only cells expressing an appropriate antigen for the antibody associated with such protein. Thus, it is not surprising that the less specific lytic peptides such as cecropins are more capable of lysing procaryotes than the eucaryotic cells of the insect.

Gram-positive procaryotes generally have a thicker cell wall than Gram-negative ones. Also, Gram-positive cell membranes have a cytoplasmic membrane and a cell wall containing mostly peptidoglycans and teichoic acids, whereas Gram-negative cell membranes have an inner cell wall consisting entirely of peptidoglycan and associated proteins surrounded by an outer cell wall comprised of lipid, lipopolysaccharide and protein. In contrast, eucaryotic cells generally have a plasma membrane comprising a lipid bilayer with proteins and carbohydrates interspersed therein, and also have organelles with their own membrane systems, but generally do not have an outer cell wall. It is readily appreciated that the considerable variation of membrane structures among bacteria (procaryotes) accounts for considerable variation in their susceptibility to lysis by the various insect immune proteins.

The variation of membrane structures among eucaryotes is also considerable, but these membranes generally comprise phospholipid molecules in a bilayer arrangement with a thickness of about 50 Å. The hydrophilic portion of the phospholipid is generally oriented to the exterior and interior surfaces of the membrane, while the hydrophobic portions are generally found in the interior region of the membrane between the hydrophilic surfaces. As reported in Nakajima et al, the presence of cholesterol and the asymmetric distribution of phospholipids in the cytoplasmic membrane of eucaryotic cells may explain the selective toxicity of sarcotoxin to bacteria. Since cholesterol causes condensation of the phospholipid bilayers, it can hinder the penetration of lytic peptides into the cytoplasmic membrane of eucaryotic cells. Similarly, the predominance of neutral phospholipids in the outer monolayer of eucaryotic membranes would result in less affinity to positively charged lytic peptides such as cecropin and sarcotoxin than acidic phospholipids generally located on the cytoplasmic side of the membrane.

Eucaryotic cells have a high degree of internal organization conferred by a complex matrix of proteins known as the cytoskeleton. Many of the proteins of the cytoskeletal matrix are anchored in the cell membrane. The degree of an intact cytoskeletal organization may determine the ability of lytic peptide to lyse the cell.

A number of the antibacterial polypeptides have been found to be useful when the genes encoding therefor are incorporated into various plant species. Particularly, when introduced into the plant genome by means of an Agrobacterium plasmid vector, the antibacterial polypeptide-encoding genes produce plant species much more resistant to certain bacterially induced disease conditions and plant pathogens. Such antibacterial polypeptides and the transformation of plants with genes encoding therefor are described in aforementioned U.S. patent application Ser. No. 889,225.

Polynucleotide molecules expressible in a given host and having the sequence araB promoter operably linked to a gene which is heterologous to such host are also known. The heterologous gene codes for a biologically active polypeptide. A genetic construct of a first genetic sequence coding for cecropin operably linked to a second genetic sequence coding for a polypeptide which is capable of suppressing the biological effect of the resulting fusion protein towards an otherwise cecropin-sensitive bacterium is also described in International Publication WO86/04356, July 31, 1986.

The Hultmark et al patents mentioned above also mention that there are no known antibodies to cecropin, indicating a wide acceptability for human and veterinary applications, including one apparently useful application for surface infections because of the high activity against pseudomonas. Similarly, EPO publication 182,278 (1986) mentions that sarcotoxins may be expected to be effective in pharmaceutical preparations and as foodstuffs additives, and that antibacterial activity of sarcotoxin can be recognized in the presence of serum. Shiba, *Chem. Abstr.* 104: 230430K (1985) also mentions preparation of an injection containing 500 mg lepidopteran, 250 mg glucose in injection water to 5 ml.

Several analogs of naturally-occurring cecropins, sarcotoxins and lepidopterans have been reported. For example, it is reported in Andreu et al, *Proc. Natl. Acad. Sci. USA*, vol. 80, pp. 6475–6479 (1983) that changes in either end of the amino acid sequence of cecropin generally result in losses in bactericidal activity in varying degrees against different bacteria. It is reported in Andreu et al (1985) mentioned above that $Trp^2$ is clearly important for bactericidal activity of cecropin, and that other changes in the 4, 6 or 8 position have different effects on different bacteria. From the data given in Table II at page 1687 of Andreu et al (1985), it appears that almost any change from natural cecropin generally adversely affects its bactericidal activity. Cecropin is defined in International Publication WO86/04356 to include bactericidally active polypeptides from any insect species and analogs, homologs, mutants, isomers and derivatives thereof having bactericidal activity from 1% of the naturally-occurring polypeptides up to 100 times or higher activity of the naturally-occurring cecropin. Other references generally discuss the effects of the α-helix conformation and the amphiphilic nature of cecropin and other lytic peptides.

It is known that lysozyme and attacins also occur in insect hemolymph. For example, it is reported in Okada et al, *Biochem. J.*, vol. 229, pp. 453–458 (1985) that lysozyme participates with sarcotoxin against bacteria, but that the bactericidal actions are diverse. Steiner et al mentioned above suggests that lysozyme plays no role in the antibacterial activity of insect hemolymph other than to remove debris following lysis of bacteria by cecropin. Merrifield et al, *Biochemistry*, vol. 21, pp. 5020–5031 (1982) and Andreu et al (1983) mentioned above state that cecropin purified from insect hemolymph may be contaminated with lysozyme, but demonstrate that the synthetically prepared cecropin is as bactericidally active as purified cecropin from insect hemolymph.

The analogs of lytic peptides known at this time are primarily conservative, point mutations of amino acids which tend to disrupt the activity of the lytic peptide. The analogs of cecropin described in the previous patent application Ser. No. 07/102,175, SB-37 and Shiva-1 are synthetic analogs which preserve the lytic activity of the natural cecropins. It would be of great utility to understand the structural properties of the known lytic peptides which relate to their diverse functional properties. With such understanding, it would then be of great utility to design and synthesize polypeptides with the specific activities desired.

Polypeptides having high lytic activity against gram positive and gram negative bacteria, fungus, yeast, protozoa, and plant or animal cells infected with pathogens, would be of great medical and agricultural importance, particularly if such polypeptides were economically and easily produced.

Polypeptides having high lytic activity against cells infected with pathogens or cancerous cells would be of great therapeutic importance in the treatment of animals.

Polypeptides having high proliferative activity would be advantageous in stimulating the immune system and in wound healing.

SUMMARY OF THE INVENTION

The present invention discloses synthetic lytic peptides, particularly designed and constructed to encompass those structural properties believed to be associated with lytic and proliferative function: aligned amphipathic α-helical conformation, with positive charge density. The synthetic lytic peptides of this invention are designed to function in the treatment of plants and animals against microbial infections including bacterial, yeast, fungal, viral and protozoan infections. These lytic peptides are also designed to function in the lysis of cancer cells.

The present invention also discloses the human Beta fibrin signal peptide and analogs as lytic peptides sharing similar structural and functional properties of the lytic peptides.

The present invention also discloses synthetic lytic peptides which stimulate cell growth and assist in the process of wound healing.

The synthetic lytic peptides of this invention also function synergistically with conventional therapeutic agents such as antibiotics and anti-cancer treatments, and may be used as general adjuvants.

Accordingly, the invention provides a method for lysing microbial and eucaryotic cells which includes contacting the cells with a lytic peptide in an amount effective to lyse the cells. The cells include gram positive and gram negative procaryotic microorganisms, lymphomas, leukemias or carcinomas, or eucaryotic cells infected with an intracellular pathogenic microorganism. The lytic peptide has from about 20 to about 40 amino acids, at least a portion of which are arranged in an aligned amphiphilic α-helical conformation. The peptide has a substantially hydrophilic head with a positive charge density and a substantially hydrophobic tail. The conformation has a predominately hydrophobic face along the length of the conformation and a predominately hydrophilic face opposed therefrom.

The invention also provides a method for selectively lysing eucaryotic cells in the presence of cells which are not lysed. The method includes contacting target eucaryotic cells in the presence of non-target cells with a selectively lytic, free peptide in an amount effective to lyse the target cells. The target cells are eucaryotic microorganisms, lymphomas, leukemias or carcinomas, or eucaryotic cells infected with an intracellular pathogenic microorganism. The lytic peptide contains from about 20 to about 40 amino acids, at least a portion of which are arranged in an aligned amphiphilic α-helical conformation with a positive charge density.

In another aspect, the invention provides a method for lysing eucaryotic microorganisms which includes contacting the eucaryotes with an amount of a lytic peptide effective to lyse the microorganisms. The peptide includes from about 20 to about 40 amino acids, at least a portion of which are arranged in an aligned α-helical conformation with a positive charge density.

In still another aspect, the invention provides a method for lysing cancer cells. The method includes contacting lymphoma, leukemia or carcinoma cells with an effective amount of a lytic peptide to lyse the cells. The peptide has from about 20 to about 40 amino acids at least a portion of which are arranged in an aligned α-helical conformation with a positive charge density.

Further, the invention provides a method for selectively lysing infected eucaryotic cells. The infected eucaryotic cells are infected with an intracellular pathogenic microorganism, such as, for example, virus, bacteria, fungi or protozoa. The method includes contacting the infected and uninfected cells with a selectively lytic, free peptide in an amount effective to selectively lyse the infected cells and leave the uninfected cells substantially free of lysis.

Still further, the invention provides a method for inhibiting eucaryotic cells in a higher animal. The method includes introducing a selectively lytic, free peptide into the higher animal in an amount effective to inhibit therein eucaryotic cells such as eucaryotic microorganisms, mammalian lymphomas, leukemias or carcinomas, or cells infected with an intracellular pathogenic microorganism.

Still further, the invention provides a method for stimulating the proliferation of normal mammalian fibroblasts and lymphocytes which includes contacting the fibroblasts or lymphocytes with a stimulating peptide of approximately 15 to 40 amino acids in an amount effective to stimulate the proliferation thereof. There is also provided a method for stimulating the proliferation of normal fibroblasts and lymphocytes in a mammal which includes introducing a stimulating peptide of approximately 15 to 40 amino acids into a mammal in an amount effective to stimulate the proliferation of fibroblasts or lymphocytes therein. This stimulating peptide contains an aligned amphipathic alpha-helical conformation with a positive charge density.

Also provided is a method for enhancing the process of wound healing in animals which includes contacting the wound with a stimulating peptide of 15 to 40 amino acids in an amount effective to enhance the healing of the wound.

In other aspects, the invention provides a synergistic composition containing lytic peptide and another therapeutic or diagnostic agent, in an amount sufficient to facilitate activity of the agent in cells.

BRIEF DESCRIPTION OF THE DRAWINGS

FIGS. 1A, 1B, and 1C illustrate the amphipathic alpha helical conformation of cecropin B; its hydrophobic and hydrophilic distribution; and its positive charge distribution.

FIGS. 3A and 3B list the amino acid sequences of the synthetic lytic peptides.

FIGS. 4A and 4B illustrate the distribution of hydrophobic and hydrophilic amino acid residues and the location of the positively charged amino acid residues for each of the synthetic lytic peptides.

FIGS. 5A to 5H, 6A to 6F, and 7A to 7D illustrate Edmunson helical wheels for the lytic peptides.

DETAILED DESCRIPTION OF THE PREFERRED EMBODIMENTS

Figure 2A:
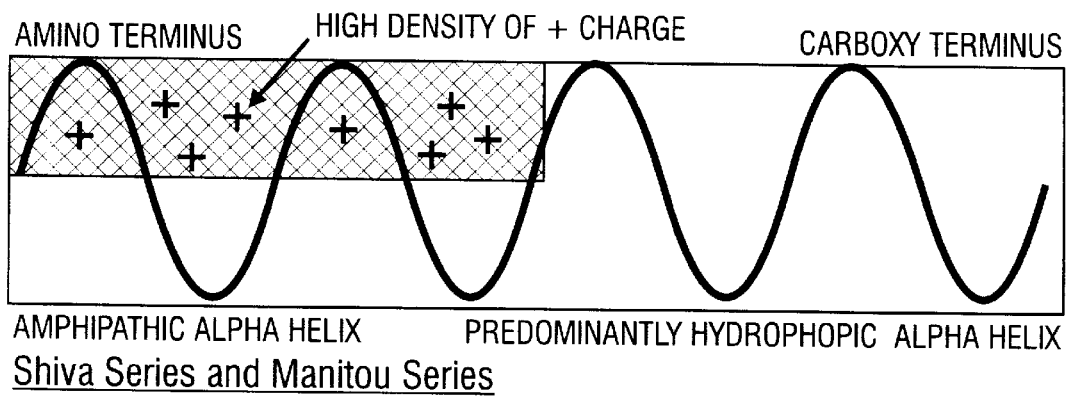
FIGS. 2A, 2B, 2C, and 2D illustrate the distribution of hydrophobicity and hydrophilicity along the alpha helix and the positive charge distribution for each class of synthetic lytic peptides.
Figure 2B:
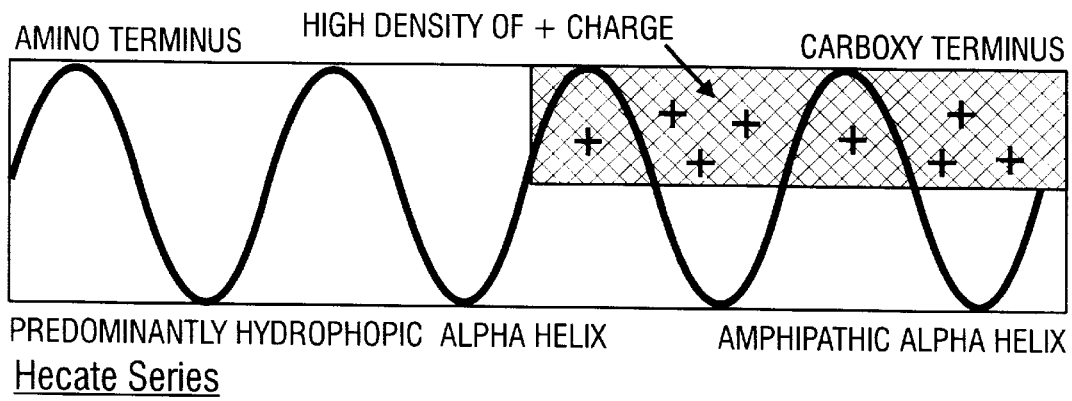
Figure 2C:
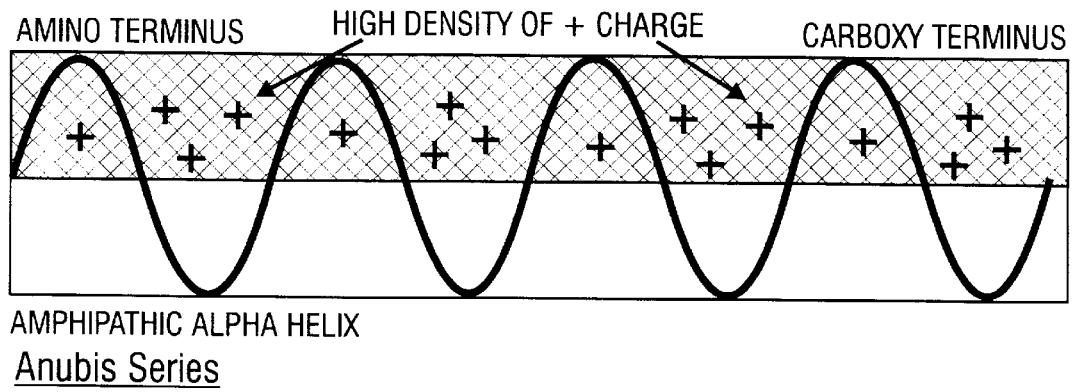
Figure 2D:
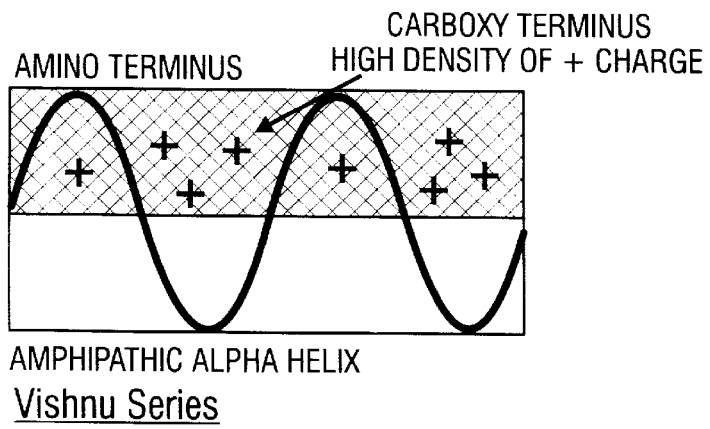

It has been found that lytic peptides having about 20–40 amino acids are capable of lysing or otherwise inhibiting bacterial or eucaryotic cells which are involved with the disease or illness of plants and animals. Such eucaryotic cells include, for example, protozoa, fungi, algae, cancer cells such as lymphomas, leukemias and carcinomas, and cells infected with intracellular fungi, bacteria, protozoa or viruses. On the other hand, certain lytic peptides of 15 to 40 amino acids have also been found to stimulate the proliferation of lymphocytes an fibroblasts; and enhance wound healing.

As used herein, the term "lytic peptide" includes any polypeptide which lyses the membrane of a cell in an in vivo or in vitro system in which such activity can be measured. Suitable lytic peptides used in the present invention have lytic activity toward one or more bacterial cells, eucaryotic cells such as protozoa, fungi, helminths, leukemias, lymphomas or carcinomas, or cells infected by intracellular pathogens. Preferred lytic peptides have from about 20 to about 40 amino acids, while preferred growth-promoting peptides have about 15–40 amino acids, at least a portion of these amino acids are arranged in an aligned α-helical conformation having a substantially hydrophilic head with a positive charge density, a substantially hydrophobic tail, and a part of opposed faces along the length of the helical conformation, one such face being predominantly hydrophilic and the other being predominantly hydrophobic. The head of this conformation may be taken as either the amine terminus end or the carboxy terminus end.

The structural features of the known lytic peptides thought to be associated with lytic function are aligned amphipathy and a substantial positive charge density.

The structural features of cecropin B are illustrated in FIG. 1. FIG. 1A demonstrates the alpha helical configuration of cecropin B, and the distribution of hydrophobic and hydrophilic amino acid residues which form its aligned amphipathic region. FIG. 1B illustrates an Edmundson wheel diagram of cecropin B, indicating an internal ring of 18 amino acids representing the amino-terminal portion of the helix and the external ring of 18 amino acids representing the carboxy-terminal portion of the molecule. The amino acids conferring positive charge to the molecule are represented by the symbol, "+".

FIG. 1C illustrates the length of the alpha helix, divided to represent two longitudinal faces of the molecule and divided again into its amino and carboxy terminal halves. The shaded portion of the figure represents the substantially hydrophilic region of the molecule while the open areas represent hydrophobic regions.

Thus FIG. 1C represents the aligned amphipathic nature of the amino terminal half of the cecropin B molecule.

An "aligned amphipathic" α-helix is defined herein as that distribution of hydrophobic and hydrophilic amino acid residues along opposing faces of the alpha-helix which results in one face of the helix being predominantly hydrophobic and the opposite face being predominantly hydrophilic. Hydrophilic amino acids are defined as those having a transfer free energy of <1.0 Kcal/mole. The following table lists the free energies of the 20 natural amino acids:

| HYDROPHOBICITY/HYDROPHILICITY | | |
|---|---|---|
| Amino Acid | Transfer Free Energy (Kcal/mole) | |
| F | 3.7 | Phenylalanine |
| M | 3.4 | Methionine |
| I | 3.1 | Isoleucine |
| L | 2.8 | Leucine |
| V | 2.6 | Valine |
| C | 2.0 | Cysteine |
| W | 1.9 | Tryptophan |
| A | 1.6 | Alanine |
| T | 1.2 | Threonine |
| G | 1.0 | Glycine |
| S | 0.6 | Serine |
| P | −0.2 | Proline |
| Y | −0.7 | Tyrosine |
| H | −3.0 | Histidine |
| Q | −4.1 | Glutamine |
| N | −4.8 | Asparagine |
| E | −8.2 | Glutamate |
| K | −8.8 | Lysine |
| D | −9.2 | Aspartate |
| R | −12.2 | Arginine |

D. M. Engelmann et al, *Annual Review of Biophyical Chemistry*, Vol. 15 330 (1986).

A "selectively lytic peptide" is a lytic peptide which preferentially lyses target cells in a system comprising both target and non-target cells, wherein the target cells are selected from bacteria, protozoa, fungi, mammalian leukemias, lymphomas and carcinomas and eucaryotic cells infected by intracellular pathogens. The selectively lytic peptides used in the present methods are preferably "free peptides," i.e. undirected in action by an antibody and otherwise unbound or unfused to another molecular fragment which adversely affects its lytic activity.

Suitable lytic peptides generally include cecropins such as cecropin A, cecropin B, cecropin D, and lepidopteran; sarcotoxins such as sarcotoxin IA, sarcotoxin IB, and sarcotoxin IC; magainin 1 and magainin 2 and other polypeptides obtainable from the hemolymph of any insect species which have lytic activity against bacteria similar to that of the cecropins and sarcotoxins. Melittin is generally not considered suitable because of its extreme toxicity. It is also contemplated that lytic peptides may be obtained as the lytically active portion of larger peptides such as attacins; lysozymes; certain phage proteins such as S protein of λ phage, E protein of PHIX 174 phage and P13 protein of P22 phage; and C9 protein of human complement. As used herein, classes of lytically active peptides such as, for example, "cecropins," "sarcotoxins" and "phage proteins," and specific peptides within such classes, are meant to include the lytically active analogues, homologues, mutants or isomers thereof unless otherwise indicated by context.

The human beta fibrin signal peptide shares common features of the known lytic peptide including significant aligned amphipathy and associated high positive density. The human beta fibrin signal peptide has now been found to share common functional properties with the lytic peptides including antibacterial and anti-cancer properties as well as the proliferative effects.

Novel synthetic lytic peptides were designed and constructed to incorporate and improve those structural features associated with lytic and proliferative activities. The essential features of these peptides include a minimal length of approximately 19 amino acids; an α helical conformation; exhibiting significant aligned amphipathy and a positive charge density.

The preferred peptides are those of 15–40 amino acids in which one or more sets of 18 linear amino acids spaced 20° apart about the axis of the helix exhibits 60–90% aligned amphipathy.

The amino acid sequence of the preferred peptides includes greater than or equal to four positively charged amino acids, such as lysine, arginine, histidine, ornithine and citrulline.

The lytic peptides of the present invention may be grouped into five structural classes according to the location of their aligned amphipathy as illustrated in FIG. 2.

Figure 4A:
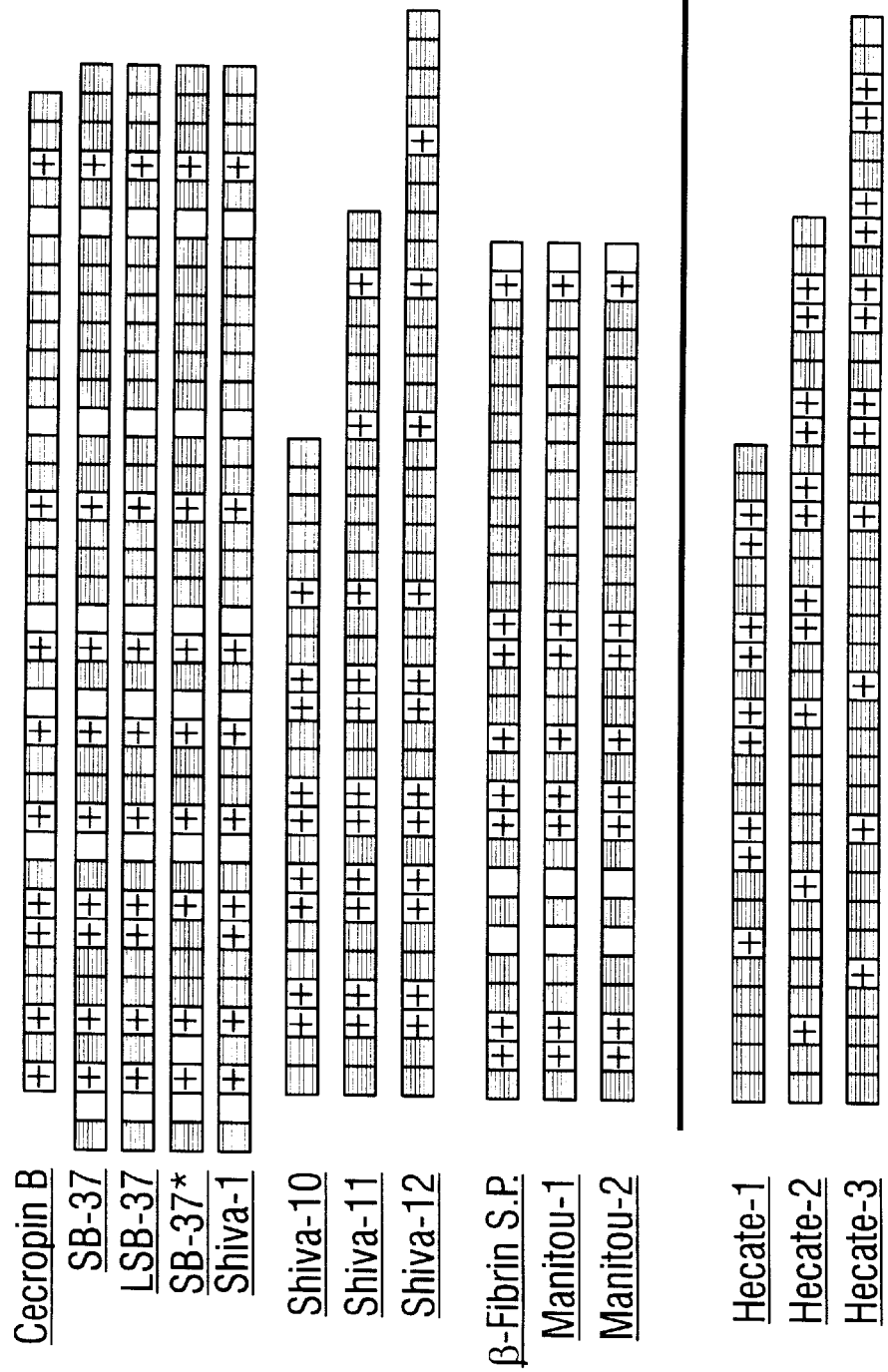
Figure 4B:
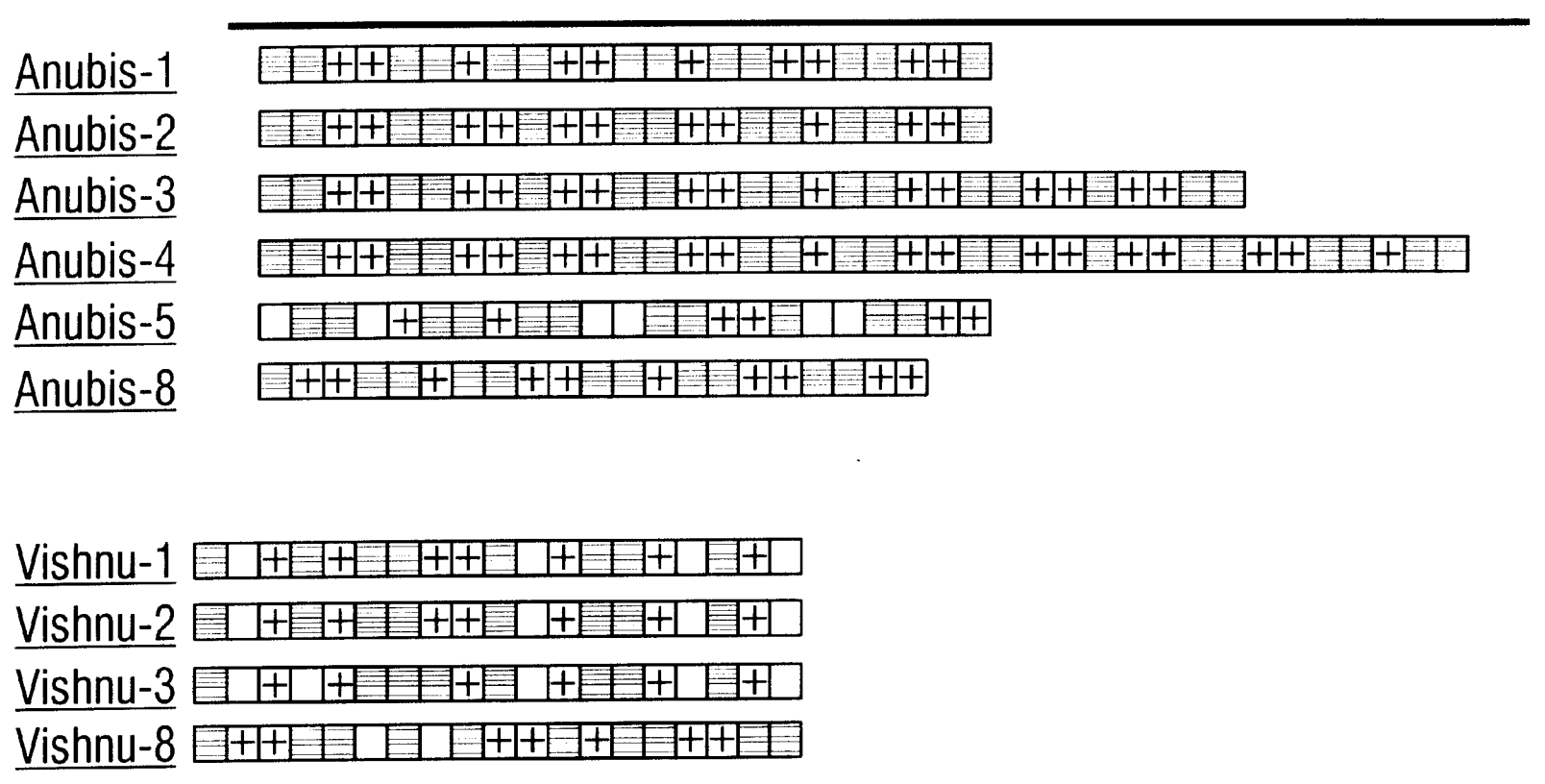
Figure 5A:
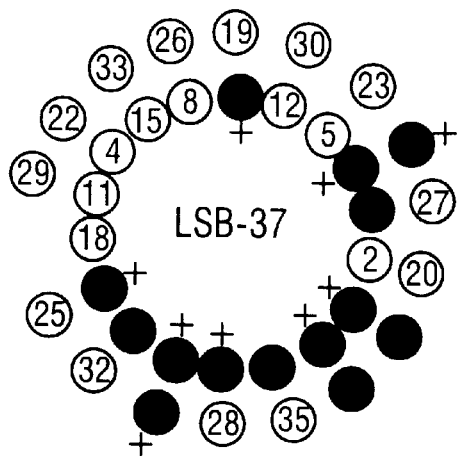
FIGS. 5A to 5H illustrate the Edmunson helical wheels of the synthetic lytic peptides.
Figure 5B:
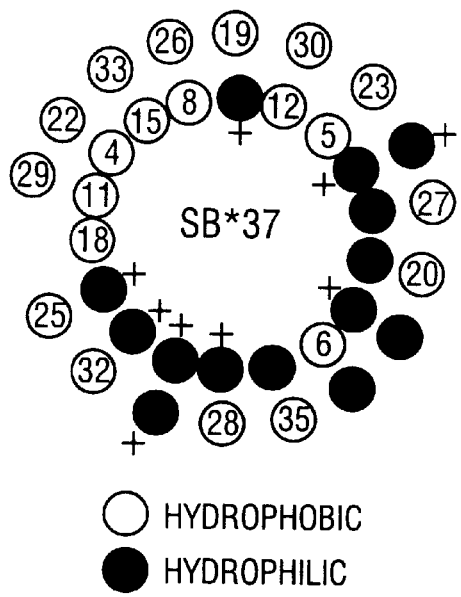
Figure 5C:
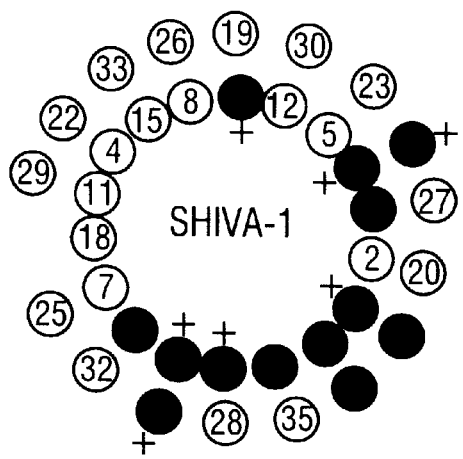
Figure 5D:
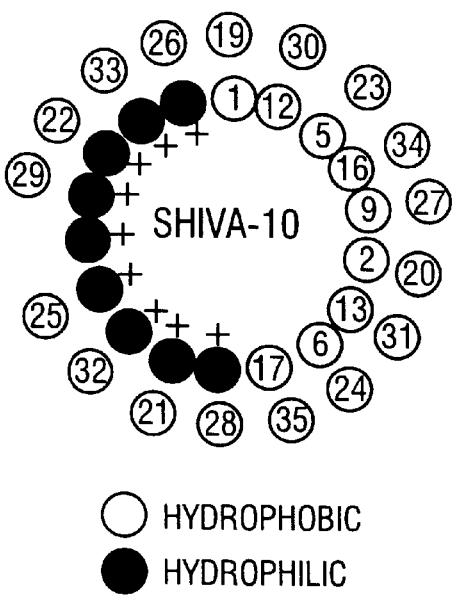
Figure 5E:
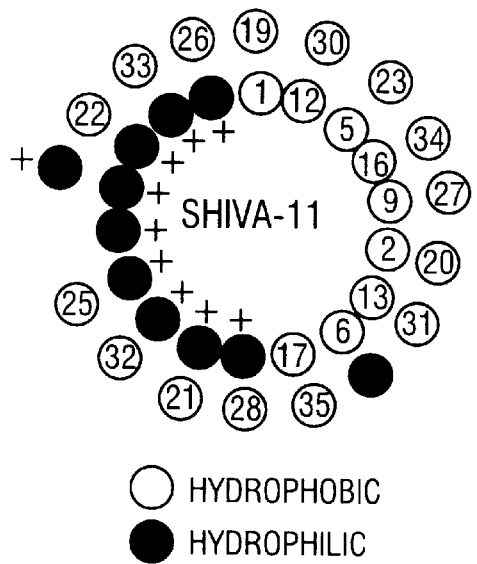
Figure 5F:
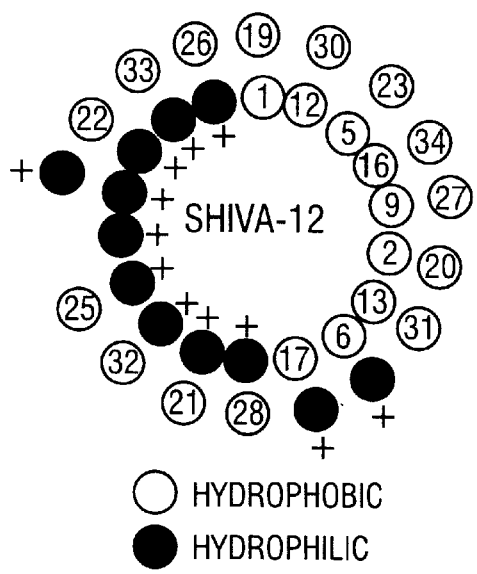
Figure 5G:
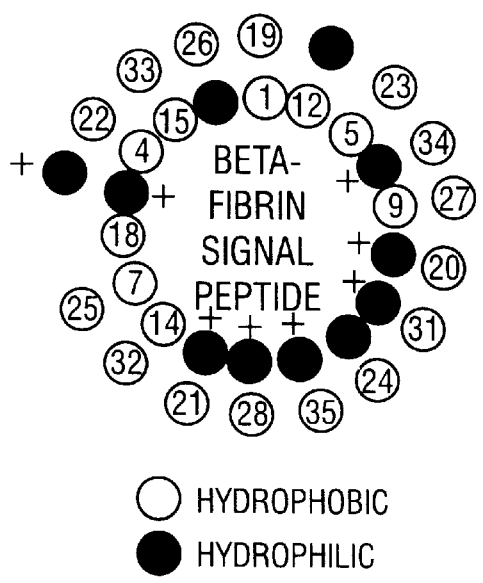
Figure 5H:
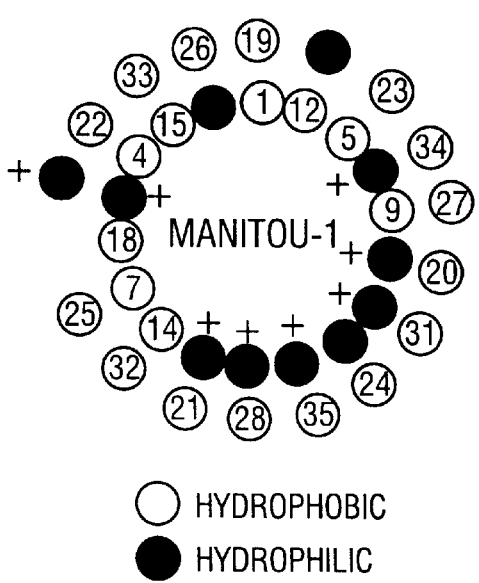
Figure 6A:
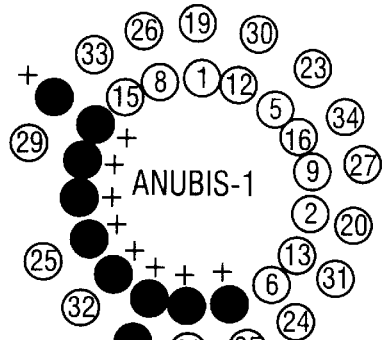
Figure 6B:
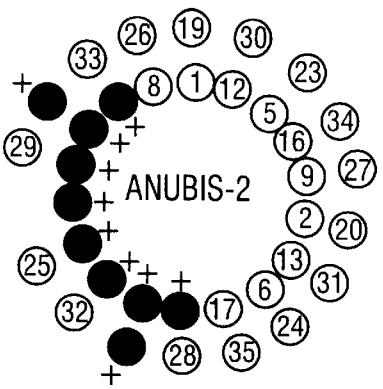
Figure 6C:
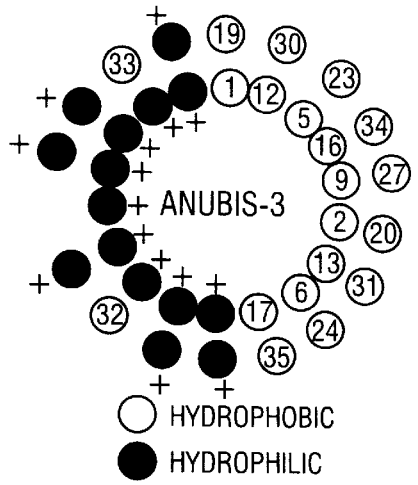
Figure 6D:
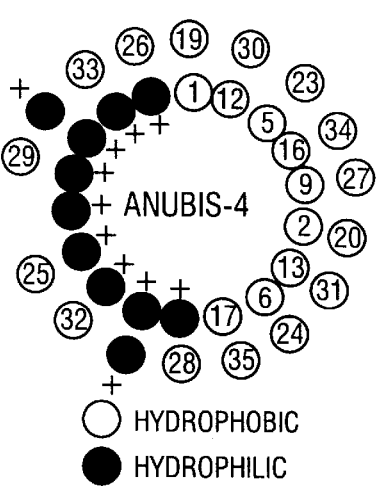
Figure 6E:
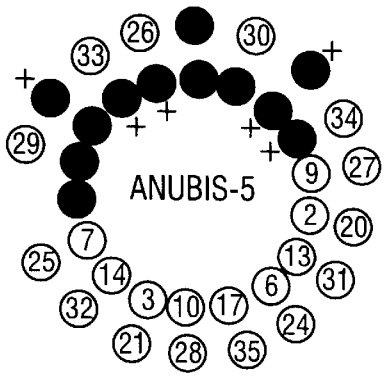
Figure 6F:
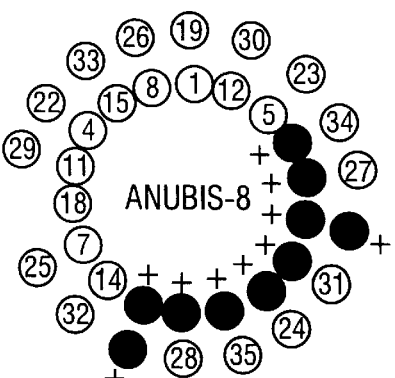
Figure 7A:
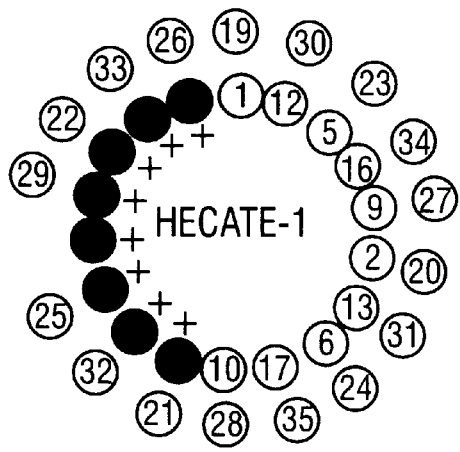
Figure 7B:
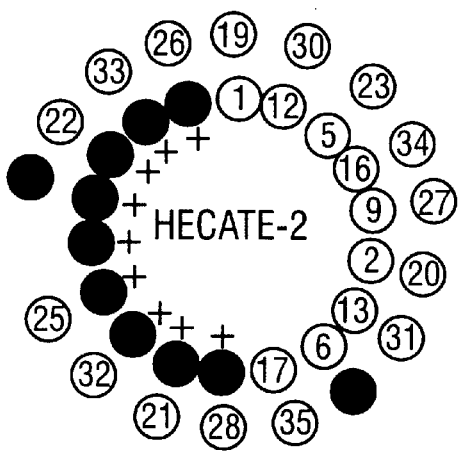
Figure 7C:
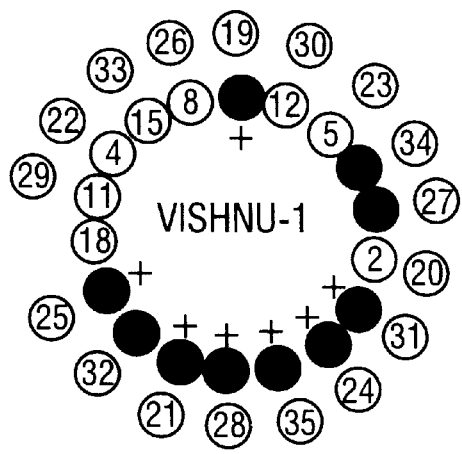
Figure 7D:
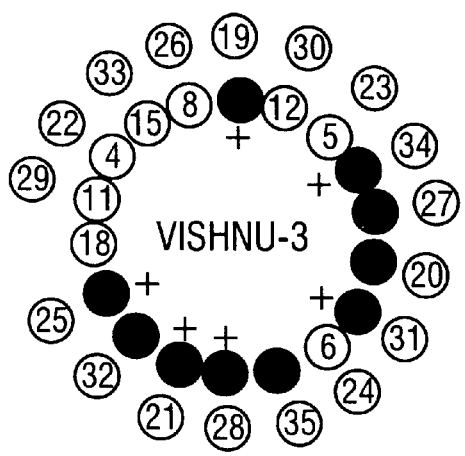

Specific peptides in each of these classes include the amino acid sequences are listed in FIG. 3, the hydrophobic/hydrophilic table in FIG. 4, and Edmundson helical wheels shown in FIGS. 5, 6 and 7.

Class No. 1—Cecropin Analogs:

Synthetic lytic peptides in the group of cecropin analogs are comprised of peptides having approximately 23 to 38 amino acids. These peptides have an aligned amphipathic region and a positive charge density distributed over the amino-terminal half of the molecule, and therefore only one set of 18 amino acids exhibiting aligned amphipathy.

The Cecropin-like class of synthetic lytic peptides comprises members such as SB37, LSB37 and LSB*37 which differ only slightly in amino acid sequence from cecropin B, and other members such as the Shiva series which differ greatly from cecropin B (approximately 50% amino acid homology). All members of this class do share a high degree of homology in hydrophobicity, amphipathy, and charge distribution.

Class No. 2—Manitou Series:

The lytic peptides classified in the Manitou series are cecropin-like analogs in that their positive charge density and aligned amphipathy is distributed over the amino terminal half of the molecule. However, included in the Manitou series is the human beta-fibrin signal peptide, which has little amino acid homology with cecropin.

Class No. 3—Anubis Series:

The synthetic lytic peptides classified in the Anubis series constitute simple, economic and easily produced peptides comprised of repeats of 3 to 5 simple amino acids chosen from the group comprising: alanine, leucine, glutamine, phenylalanine and lysine. It is anticipated that other amino acids may also be used, providing the essential structural properties of the polypeptide is maintained. These peptides have little or no amino acid homology to the natural magainins, however, the aligned amphipathy and positive charge density is highly homologous. The peptides of the Anubis series have a total length of approximately 21 to 38 amino acids, and are comprised of two sets of 18 linear amino acids exhibiting aligned amphipathy.

Class No. 4—Hecate Series:

The Hecate Series is also comprised of simple combinations of 3 to 5 amino acids. The peptides in this series have varied lengths of amino acids forming the hydrophilic tail of the molecule.

The lytic peptides in the Hecate series are comprised of peptides having an aligned amphipathic region and positive charge density distributed over the carboxy terminal half of the molecule in a manner homologous to the lytic peptide melittin, but with little or no amino acid homology to the known peptide. The lytic peptides in this series are of approximately 23 to 38 amino acids in length, with the carboxy terminal amino acid designated as number 1. These peptides contain one set of 18 linear amino acids exhibiting aligned amphipathy.

Class No. 5—Vishnu Series:

The Vishnu Series is comprised of the amino-terminal half of the cecropin-like analogs. The amino acid sequence is identical to the first 19 amino acids of these peptides. Vishnu peptides are "halfmers" of the cecropin analogs and have little or no lytic activity.

It is contemplated that the shortened length of the molecules may not enable lytic function, as the 19 amino acid helix may not span the cell membrane.

The synthetic peptides of the Vishnu series are comprised of the amino terminal half of the cecropin analogs. These peptides are approximately 19 amino acids in length and have complete aligned amphipathy, no hydrophobic tail, and have a positive charge density distributed throughout the molecule. There are no known natural analogs to this series.

While the specific amino acid structure of the lytic peptides was found not to be critical for lytic function, the hydrophobic/hydrophilic amino acid and positively charged amino acid distribution was found to be highly significant.

The hydrophobic/hydrophilic amino acid and positively-charged amino acid distribution of synthetic lytic peptides and their comparison to cecropin B is illustrated in FIG. 4.

It is anticipated that conservative substitutions for these amino acids may include D and L forms and synthetic amino acids such as ornithine, citrulline, and homoserine, provided that the essential structural features are maintained.

The lytic peptides of the present invention are effective in lysing various types of bacterial and eucaryotic cells such as gram positive and gram negative bacteria, eucaryotic microorganisms, mammalian neoplastic cells and cells infected with intracellular pathogenic microorganisms. Eucaryotic microorganisms include, for example, fungi, yeasts, and protozoans such as sarcodina, mastigophora, ciliata and sporozoa. The lytic peptides are particularly effective against $Trypanosoma$ $cruzi$ and $Plasmodium$ $falciparum$ which are the causitive agents of Chagas disease and malaria, respectively, and are also contemplated as being particularly effective against $Trypanosoma$ $gambiense$ which is the causative agent of African sleeping sickness. The method of the present invention is useful to lyse or inhibit cancer cells such as lymphomas, leukemias and carcinomas, and particularly mammalian cancer cells of these types.

Suitable infected eucaryotes subject to lysis or inhibition according to the present method include cells infected with intracellular pathogenic microorganisms such as viruses, bacteria,.fungi, or protozoans. Specific representative examples of such pathogens, the host cells of which are contemplated as suitable for lysis or inhibition according to the present method, include protozoa such as $P.$ $falciparum,$ $T.$ $cruzi,$ bacteria such as $Listeria$ $monocytogenes,$ $Brucella$ $abortus$ and viruses such as parainfluenza, measles, HIV, and herpes simplex II. The method is particularly effective for the treatment of HIV and herpes virus-infected cells. Such pathogens grow or replicate within the infected cell and are generally protected from inhibition or lysis by the membrane of the host cell. However, the method of the present invention results in lysis of the host cell so that the intracellular pathogen is subsequently destroyed or subject to lysis or inhibition with the lytic peptides of the present invention or another inhibiting agent since it is no longer protected by the host cell membrane.

In accordance with the present method, the lytic peptide is used to lyse or otherwise inhibit eucaryotic cells by contacting the cells with the peptide. The amount of the lytic peptide necessary to induce cell lysis will usually be at least 0.1 $\mu$M, and preferentially 50–100 $\mu$M.

In a system in which the cells contacted with the lytic peptide are cultured or grown for obtaining biological or biochemical products therefrom, a cytoplasmic product may be desirably recovered from the lysed cells. For example, the recovery of a product such as interferon may be facilitated by treating cells producing the interferon product with a lytic peptide in combination with cytoskeletal formation inhibitors such as cytochalasin B, avoiding the use of detergents which complicates purification of the desired product.

In a preferred embodiment, the target cells to be lysed are lysed or otherwise inhibited in the presence of non-target cells. For example, the target cells may be an in vitro culture, mixture, or suspension, or may be target cells in a higher animal host, particularly chordate animals and chordate or nonchordate aquacultural animals, and especially mammals such as man. In such a situation, some degree of care is exercised in the selection of the lytic peptide and its concentration to avoid substantial lysis or inhibition of the non-target cells. For use in vivo, an amount of lytic peptide in the range of from about 1 mg/kg to about 100 mg/kg is usually sufficient to effect the desired inhibition and avoid substantial inhibition of the non-target or host cells, although this dosage may be increased or decreased, or repeated in a series of applications. The peptide may be introduced directly into the higher animal in any conventional manner, e.g. by injection of the peptide in a pharmaceutically acceptable carrier intramuscularly, subcutaneously, intravenously, or intraperitoneally, and preferably at or near the site of infection or cancer. Where there may be a relatively high incidence of target cells in a host, particularly in advanced stages of infection or cancer, additional caution should be exercised since rapid lysis of such a large number of target cells may induce a host reaction to the products of the lytic or inhibitory activity.

Although the present invention is not bound or limited by theory, it is believed that the membranes of the lower eucaryotes are generally subject to lysis by lytic peptides because of the differences in their membranes and cytoskeletal components. However, the membranes of normal cells of the higher eucaryotes somehow prevent lysis, possibly for example, by the ability of their well-developed cytoskeletons to quickly repair any membrane damage caused by the lytic peptide. On the other hand, higher eucaryotic cells with an aberrant cytoskeleton, such as neoplastic or infected cells, are generally unable to prevent lysis by the lytic peptide in the present method.

Quite unexpectedly, it has also been found that the lytic peptide can also stimulate the proliferation of fibroblasts and mitogen activated lymphocytes by contacting the lymphocytes or fibroblasts with an effective amount of a stimulating peptide. As used herein, the term "stimulating peptide" includes not only the preferred lytic peptides described hereinabove having from about 20 to about 40 amino acids, but also includes such peptides having fewer than 20 or more than 40 amino acids containing an active form of the portion of such lytic peptides inducing such stimulation, whether or not they are lytically active. Preferred stimulating peptides include peptides having the first approximately 15–20 amino acids from the amine terminus of lytic peptides such as cecropins and sarcotoxins. In this sense, "stimulation" means an enhancement of proliferation in any system in which it can be observed or measured, and the stimulating property of such peptides may or may not be related to their lytic property. For convenience, reference is made hereinbelow to cecropin by way of example with the understanding that other stimulating peptides may be used.

Generally, lymphocytes must be activated by a mitogen, or an antigen reactive with antibodies expressed by the lymphocytes, before any stimulation thereof by a stimulating peptide such as cecropin. Mitogens include, for example, phytohemaglutinin, pokeweed mitogen, concanavilin A, substances for which lymphocytes have developed "memory" such as tetanus toxoid, and the like. Thus, in one embodiment, activated lymphocytes (e.g., lymphocytes in the presence of a mitogen) or fibroblasts are contacted with a stimulating peptide in vitro to increase proliferation thereof. In this manner, the production of biological products by lymphocytes, for example, such as interferon and interleukin-2, may be enhanced by culturing the lymphocytes in the presence of, for example, pokeweed mitogen and cecropin.

In accordance with this embodiment, the lymphocytes or fibroblasts to be stimulated are contacted with an effective amount of stimulating peptide, generally an amount sufficient to provide a concentration in the medium containing the lymphocytes or fibroblasts of from about 1 to about 50 $\mu$M. In a preferred embodiment in which the stimulating peptides are administered in vivo, contemplated dosages of the peptides range from about one to about 10 mg/kg. The peptide may be introduced into the animal to be treated by injection in a suitable pharmaceutical carrier such as saline solution, for example, intramuscularly, subcutaneously, intravenously or intraperitoneally, preferably at or near the site where such stimulation is desired, e.g. a wound, graft, injury or infection. The treatment may be repeated as necessary to sustain the proliferative stimulation of the lymphocytes or fibroblasts.

Although the present invention is not bound or limited by any theory, it is believed that the stimulation of fibroblasts and lymphocytes results from the binding of the amphipathic, α-helical amine terminus portion or end of the preferred lytic peptide to lymphocyte and fibroblast cell membranes. No binding activity is believed to be associated with the generally hydrophobic tail or carboxy terminus end or portion of cecropin or sarcotoxin. Thus, where lytic activity is not beneficial or desired, lymphocytes and/or fibroblasts can be stimulated by a shorter peptide from which the hydrophobic tail has been removed, i.e. the remaining head including the first 15–25, and preferably the first 18–20 amino acids in the cecropin or sarcotoxin sequence.

In another embodiment of the invention, a lytic and/or stimulating peptide is introduced into a higher animal by placing cells into the animal which have an expressible gene coding for the peptide. Such cells may be prepared by genetically transforming cells such as bone marrow cells, embryos, hematopoietic stem cells, and the like. Techniques for such transformation are well known in the art and include, for example transfection with retroviral vectors, electroporation, microinjection and the like.

The synthetic peptides of this invention comprise peptides of greater than or equal to 19 amino acids having a significant portion of the molecule amphipatic with a positive charge density over the amphipatic region.

The amino acid homology of peptides can be readily determined by contrasting the amino acid sequences thereof as is known in the art. Similarly, the amphiphilic homology of peptides can be determined by contrasting the hydophilicity and hydrophobicity of the amino acid sequences. The amino acid sequences of various preferred lytic peptides are compared in FIG. 3.

EXAMPLE 1

Synthesis of Lytic Peptides

The lytic peptides were synthesized on a Biosearch Sam Two peptide synthesizer using 4-methyl benzhydrol amine (MBHA) resin with a carboxy-terminal amide. All reagents used in the biosynthesis were obtained from Biosearch, San Rafael, Calif.

After extraction and Sephadex column chromatography, the purity of the peptides was determined by high pressure liquid chromatography (HPLC) on Varian 5000 HPLC unit. A Waters $\mu$Bondepak C18 column, 8 mm×10 cm Radial-Pak cartridge, employing the Radial Compression Module-100 was utilized. HPLC profiles of the synthesized peptides indicated a purity of more than 95%.

To determine that the syntheses had progressed to completion, amino-terminus sequence analysis was performed on all peptides using an Applied Biosystems 470-A gas phase protein sequencer. PTH-derivitized amino acids generated from the sequencer were analyzed in a Waters Pico Tag system employing a C18 column, 3.8 mm×15 cm (Waters Nova-Pak).

The lytic peptides of this invention were synthesized by these methods. A listing of the amino acid sequences of these peptides is found in FIG. 3.

EXAMPLE 2

Antibacterial Function of the Lytic Peptides Shiva-1, LSB-37, and Anubis-8

The antimicrobial activity of the lytic peptides was tested using the MBC and MIC susceptibility tests described by Schoenknecht et al, *Manual of Clinical Microbiology*, 4th ed., E. H. Lennett et al, eds. Am. Soc. for Microbiology, Washington, D.C., p. 1000 (1985), which is hereby incorporated by reference.

Bacteria were subcultured onto Muller-Hinton (MH) agar plates and incubated overnight at 35° C. A tube containing 3 ml Muller-Hinton Broth was inoculated with 5 or more colonies from the plate to achieve a turbidity equivalent of a No. 1 McFarland standard (approximately $10^2$ organisms per ml). A volume of 0.1 ml of the turbid inoculum was transferred to 10 ml of MHB and incubated in a shaking water bath at 35° C. until turbid. Twofold serial dilutions of the lytic peptides were made in 2 ml of MHB, and the bacteria were standardized to equal 0.5 McFarland turbidity standard ($5\times10^7$ organisms per ml) in a 3 ml of broth. The inoculum was then diluted 1/10 to $5\times10^6$ organisms per ml. A 100 $\mu$l sample of the diluted inoculum was placed into tubes containing serial dilutions of the lytic peptides. The final inoculum of approximately $2.5\times10^5$ organisms per ml, was then incubated at 35° C. for 20 hours. Tubes without visible growth were vortexed vigorously for 15 seconds and reincubated an additional 4 hours. Tubes were then mixed again, and a 0.1 ml sample was spread on the surface of dried Trypticase soy agar plates and incubated overnight at 35° C. for MBC determination. After incubation, the number of colonies per plate were counted, and compared with the number of colonies per plate for the original inoculum. The number of colonies that represent 0.1% of the original inoculum was determined, and any number less than or equal to 0.1% of the original inoculum was considered to be a 99.9% bactericidal kill.

An additional dilution of the inoculum in MHB to achieve a concentration of $5\times10^2$ organisms per ml was made, and 0.1 ml of this suspension was spread onto MH agar plates with a sterile, bent glass rod. The samples were prepared in duplicate and incubated overnight at 35° C. The next day, the lowest concentration of the lytic peptide at which no growth of bacteria was detected on the agar plates was recorded as the MIC.

To a 1.5 ml Eppendorf tube was added 50 μl of the bacteria under investigation and 50 μl of 0.01 M phosphate buffered saline (PBS), pH 7.0. The bacterial cells were collected in late log phase growth and incubated at room temperature for one hour and then at 37° for 30 minutes in the presence of 0.01–10 μM lytic peptide. At the end of the incubation, the treated bacteria were diluted 1:1000 and 100 μl of this dilution was plated onto Tryptose agar growth plates. The plates were then incubated for three days at 37° C. The test plates were then examined, colony counts were made, and MBC values calculated.

An MBC value less than 50 μM is indicative of an effective antimicrobial agent.

The results of treatment with the lytic peptides LSB 37, Shiva-1, Anubis-8 and Vishnu-3 on the gram negative (−) bacteria E. Coli, P. aeruginosa, and the gram positive (+) bacteria S. aureus are shown in Table I.

TABLE I

|  | E. coli (−) | P. aeruginosa (−) | S. auerus (+) |
|---|---|---|---|
| LSB-37 | 16 μM | 8 μM | 64 μM |
| Shiva-1 | 2 μM | 4 μM | 32 μM |
| Anubis-8 | 16 μM | 16 μM | 8 μM |
| Vishnu-3 | >64 | >64 | >64 |

EXAMPLE 3

Antibacterial Functions of the Lytic Peptides LSB-37 and Anubis-2

The procedure of example 2 was followed using a variety of freshly isolated bacterial samples. The MIC and MBC results are indicated in Table II.

TABLE II

|  | LSB-37 | | Anubis-2 | |
|---|---|---|---|---|
|  | MIC (μM) | MBC (μM) | MIC (μM) | MBC (μM) |
| Bacteria |  |  |  |  |
| Acinetobacter Cal Anit | 0.5 | 1 | 3.2 | 3.2 |
| Citrobacter Diversus | 1 | 4 | 3.2 | 6.4 |
| Citrobacter Freundii | 1 | 4 | 3.2 | 6.4 |
| Enterobacteria Cloacae | 2 | 8 | 6.4 | 12.8 |
| Eschera Coli | 1 | 4 | 6.4 | 12.8 |
| Klebsiella pheumoniae | 2 | 8 | 3.2 | 6.4 |
| Klebsiella pheumoniae-2 | 4 | 8 | 6.4 | 25.6 |
| Morganella morganil | 32 | — | 51.2 | — |
| Pseudomonas aeruginosa-1 | 8 | 16 | 6.4 | 25.6 |
| Pseudomonas aeruginosa-2 | 4 | 16 | 3.2 | 6.4 |
| Pseudomonas aeruginosa-3 | 8 | 16 | 6.4 | 51.2 |
| Serratia Marcescens | 32 | — | 51.2 | — |
| Gram Positive Bacteria |  |  |  |  |
| Enterococcus-1 | 8 | 32 | 1.6 | 3.2 |
| Enterococcus-2 | 32 | — | 51.2 | — |
| Enterococcus-3 | 32 | — | 51.2 | — |
| Staph aureus | 32 | — | 6.4 | 51.2 |
| Staph Coag neg | 32 | — | 1.6 | 3.2 |
| Staph auerus-MR-1 | n.a. | — | — | 51.2 | — |
| Staph aureus-MR-2 | n.a. | — | — | 12.8 | 25.6 |

—Data not available.

EXAMPLE 4

Lytic Peptides Lyse Bacteria

The method of example 2 was followed to test the effectiveness of the synthetic lytic peptides on bacterial cells. The results are shown in Table III, and represent MBC values (μM). A NBC value>approximately 50 μM is considered an effective bacterial inhibitor.

TABLE III

|  | E. coli (−) | P. aeruginosa (−) | S. auerus (+) |
|---|---|---|---|
| Cecropin-B | 4.5 | 4.2 | 68 |
| SB-37 | 2.0 | 3.5 | 64 |
| LSB-37 | 2.0 | 3.6 | 64 |
| Shiva-1 | 4.0 | 4.5 | 64 |
| Shiva-10 | 1.0 | 2.0 | NA |
| Manitou-1 | 8 | 16 | 32 |
| Hecate-1 | 4.0 | 10.0 | NA |

EXAMPLE 5

Treatment of Bacterial Infection in Catfish By Injection of Synthetic Lytic Peptides Catfish fingerlings weighing approximately 2 oz. were pretreated with $5 \times 10^6$ cells of the bacteria Edwardsiella ictaluri. Treatment groups of the fish were then injected intraperitoneally (i.p.) with the lytic peptide LSB-37 dissolved in saline, or a saline control once per day for a period of 4 days. The survival rates and the bacteria counts in the liver of the autopsied fish indicated that the lytic peptide LSB-37 was successful in reducing the lethal effects of E. ictaluri bacterial infection in catfish. These data are shown in Table IV.

TABLE IV

LSB-37 Treatment of Catfish Fingerlings Infected With Edwardesiella Ictaluri

| Treatment | % Survival | # Bacteria/g Liver |
|---|---|---|
| Non-infected Saline control | 85 | N.A. |
| Non-infected + 200 μg LSB-37 | 100 | N.A. |
| Infected Saline controls | 10 | $4.8 \times 10^6$ |
| Infected <20 μg LSB-37 | 25 | $4.2 \times 10^6$ |
| Infected <100 μg LSB-37 | 30 | $2.1 \times 10^6$ |
| Infected <200 μg LSB-37 | 55 | $0.8 \times 10^6$ |

EXAMPLE 6

Synthetic Lytic Peptides Lyse Cancer Cells

EL-4 lymphoma cells obtained from ATCC were suspended in RPMI 1640 growth medium at a density of $5 \times 10^6$ cells per 100 μl in microtiter test plates. Various concentrations of lytic peptides in a total volume of 10 μl were added, and the test plates incubated at 37° C. in 5% $CO_2$ for one hour. Cell viability was then determined by trypan blue exclusion. The results shown in Table V indicate synthetic lytic peptides kill cancer cells.

TABLE V

| | % EL-4 Cells Killed | | | |
|---|---|---|---|---|
| Concentration (μM) | LSB-37 | LSB*37 | Shiva-1 | Manitou-1 |
| 10 | N.D. | N.D. | 2 | 5 |
| 25 | 2 | 2 | 18 | 28 |
| 50 | 5 | 10 | 42 | 78 |
| 100 | 38 | 45 | 87 | 100 |

B-16 myeloma cells and normal 3T3 human fibroblasts were either permitted to attach to the test plate, or treated with trypsin to free the cells from the plastic dish prior to treatment. Cells were then treated with 100 µM lytic peptide for one hour as described above, and cell viability was then determined by trypan blue exclusion. The results are shown in Table VI.

TABLE VI

% B-16 Cell Viability

| | Control | LSB-37 | Manitou-1 |
|---|---|---|---|
| 3T3 Monolayer | 96 | 94 | 85 |
| B-16 Monolayer | 94 | 78 | 19 |
| 3T3 Suspension | 98 | 12 | 5 |
| B-16 Suspension | 96 | 22 | 0 |

These data indicate both Manitou-1 and LSB-37 are able to lyse trypsinized normal 3T3 Fibroblasts and B-16 cancer cells, in suspension culture. However, when cells are attached to the growth plate in a monolayer culture, Manitou-1 is more effective than LSB-37 in selectively killing cancer cells. The killing of normal 3T3 fibroblasts in suspension culture is thought to be due to disruption of cell membrane by treatment with trypsin.

EXAMPLE 7

The Role of Cytoskeletal Structure in Susceptability To Lysis

Primary fetal donkey dermal cells (FDD) were treated to assess the effects of cold and cytoskeletal inhibitors on cellular resistance to lytic peptides, to substantiate the hypothesis that a weakened cytoskeletal system renders a normally resistent cell susceptible to the lytic activities of the lytic peptides.

In the first treatment group, FDD were chilled to 4° C. for 15 minutes and then exposed to 100 µM lytic peptide for an additional 15 minutes at 4° C. The cells were then washed, and incubated for 45–60 minutes in fresh DMEM medium.

A second test group of FDD was placed in medium containing either cytochalasin-D (5 µg/ml) or colchicine (0.1 µg/ml) and incubated at 37° C. for 15 minutes. The cells were then exposed to 100 µM lytic peptide for an additional 15 minutes, washed and incubated 45–60 minutes in fresh DMEM medium at 37° C.

The third test group of FDD cells was incubated for 15 minutes at 37° C., exposed to 100 µM lytic peptide for 15 minutes, washed, and incubated an additional 45–60 minutes in fresh DMEM medium at 37° C. At the end of the incubation period, cell counts were made by trypan blue exclusion, and the percent viability calculated. The results are shown in Table VIII, and indicate that treatment with the cytoskeletal inhibitors colchicine and cytochalasin D, or cold treatment significantly enhances the lytic ability of the peptides.

TABLE VII

% Viability of Treated DD Cells

| Treatment Group | LSB-37 | Manitou-1 |
|---|---|---|
| Control, no peptide | 98 | 96 |
| Warm-treated | 96 | 78 |
| Cold-treated | 70 | 8 |
| Colchicine-treated | 40 | 30 |
| Cytochalasin D-treated | 32 | 23 |

EXAMPLE 8

Proliferative Activity of Synthetic Lytic Peptides

Human mononuclear leukocytes were isolated from whole blood in the following manner. Blood was collected in vacutainer tubes containing EDTA, and was then diluted with an equal volume of calcium and magnesium-free PBS and layered over Histopaque resin (GIBCO). The tubes were centrifuged for 30 minutes at 25° C. and 450×g. The plasma and platelets above the banded layer of cells in the resulting gradient were removed and discarded. The banded white blood cells were removed to fresh test tubes, washed 3 times with PBS, and resuspended in RPMI medium containing 10% fetal bovine serum (FBS), mercaptoethanol, and penicillin and streptomycin as antibiotics. The cells were then counted and resuspended to a final concentration of $3 \times 10^6$ cells/ml.

To each well of a 96 well flat-bottomed microtiter plate was added 100 µl of cells ($3 \times 10^5$ cells). Treatment groups were set in quadruplicate samples. The appropriate concentration of test peptide and/or the mitogen phytohemaglutinate (PHA), was added in a total volume of 100 µl of medium to the test wells. The plates were then incubated at 37° C. and 5% CO2 for a duration of 72 hours. At the end of the incubation period, 1 µCi of 3H-thymidine in 1 µl TRIS-HCI, PH8 was added to each well, and the plates incubated an additional 18 hours.

Cellular DNA was harvested onto glass fiber filters using a semi-automatic cell harvestor. The glass filters were then placed into vials containing scintillation fluid, and the samples were counted in a scintillation counter. The uptake of 3H-thymidine is an indicator of cell proliferation, thus the higher the number of counts in the sample, the greater the proliferative activity of the cells. The results in Table XI indicate that low dose of the synthetic peptides of this invention stimulate cell growth. The data also suggest that the lytic peptides may interact synergistically with other chemical agents, such as PHA to enhance their activity.

TABLE VIII $^3$H-Thymidine Uptake in WBC
% of Control

| | | PHA (mg) | | |
|---|---|---|---|---|
| | | 0 | 0.5 | 5.0 |
| Manitou-1 | 10 | 239 | 191 | 125 |
| (µM) | 25 | 325 | 153 | 143 |
| | 50 | 62 | 61 | 63 |
| | 100 | 39 | 8 | 0 |
| Anubis-2 | 10 | 149 | 290 | 120 |
| (µM) | 25 | 46 | 393 | 108 |
| | 50 | 19 | 4 | 1 |
| | 100 | 26 | 5 | 0 |

EXAMPLE 9

Proliferation of Lymphocytes by Treatment with Lytic Peptides and Synergistic Activity with Tetanus Toxin White blood cells were isolated as described in Example 8 from a person who had received a tetanus shot during the previous 6 months. It was expected that some of the lymphocytes would thus respond to the exogenous tetanus toxin with proliferation. The lymphocytes were prepared and incubated as described for example 8 in the presence of the appropriate concentration of Tetanus Toxin (0–4.0 µg/µl and/or lytic peptide (10–100 µM). At the end of the incubation period, cells were counted by trypan blue exclusion, and the data expressed as percent of control (no treatment). These data are shown in Table IX, and indicate that the peptide Vishnu-3, which is devoid of lytic activity, is a potent stimulator of cell proliferation. These data also suggest that the lytic peptides may be utilized as general adjuvants.

TABLE IX

PROLIFERATION OF LYMPHOCYTES (% OF CONTROL)

| | | Tetanus Toxin ($\mu$g/$\mu$l) | | | |
|---|---|---|---|---|---|
| | | 0 | 0.5 | 1.0 | 2.0 | 4.0 |
| Vishnu-3 ($\mu$M) | 10 | 170 | 50 | 125 | 155 | 110 |
| | 25 | 210 | 155 | 145 | 150 | 140 |
| | 50 | 160 | 150 | 140 | 135 | 135 |
| | 100 | 200 | 175 | 140 | 165 | 155 |
| LSB-37 ($\mu$M) | 10 | 150 | 170 | 145 | 130 | 140 |
| | 25 | 170 | 150 | 190 | 140 | 170 |
| | 50 | 120 | 220 | 240 | 250 | 225 |
| | 100 | 50 | 50 | 50 | 50 | 50 |

EXAMPLE 10

Synergy of Lytic Peptides With Antibiotics

The synergy of the lytic peptides was examined by incubating bacterial cells in the presence of both a lytic peptide and a known antibiotic according to the methods described for Example 2. At the end of the incubation period, cell counts were made, and the percent viability of the bacterial cells was calculated. The results are shown in Table X, and suggest synergistic action of Manitou-1 and streptomycin in $E.$ $Coli$.

TABLE X

| Antibiotic ($\mu$M) | Manitou-1 ($\mu$M) | | | |
|---|---|---|---|---|
| | % Cell Death In $E.$ $coli$ | | | |
| | 0 | 0.01 | 0.10 | 1.0 |
| Control - 0 | 0 | 0 | 0 | 0 |
| Tetracycline - 0.5 | 0 | 68 | 0 | 0 |
| Tetracycline - 5.0 | 58 | 88 | 58 | 47 |
| Streptomycin - 0.5 | 0 | 99.9 | 68 | 0 |
| Streptomycin - 5.0 | 87 | 58 | 99.9 | 99.9 |
| | % Cell Death In $S.$ $auerus$ | | | |
| | 0 | 0.01 | 0.10 | 1.0 |
| Control - 0 | 0 | 0 | 0 | 0 |
| Tetracycline - 0.5 | 0 | 0 | 0 | 0 |
| Tetracycline - 5.0 | 35 | 35 | 35 | 35 |
| Streptomycin - 0.5 | 0 | 0 | 0 | 0 |
| Streptomycin - 5.0 | 87 | 87 | 95 | 86 |

EXAMPLE 11

Wound Healing

To evaluate the ability of the lytic peptide LSB-37 to limit the growth, as well as the septicemic disease associated with $Pseudomonas$ $aeurginosa$ infection, the following protocol was followed.

Thirty-five Sprague Dawley female rats weighing between 200 and 300 grams were anesthetized, the hair on their backs was clipped, and they were secured in an apparatus which allowed for selective exposure of approximately 20% of their skin surface area to a 10 second exposure to boiling water. This model, developed by Walker and Mason (Journal of Trauma, Vol. 8, pages 1049–1051, 1968) is an established standard procedure in burn trauma research. The model consistently results in uniform full thickness skin burn.

Immediately following the burning, rats were divided into seven test groups of five rats each, and housed in seven cages. In six groups, the burned skin was seeded with 1.0 ml of PBS containing $1 \times 10^6$ cells of $Pseudomonas$ $aeruginosa$ (supplied by Dr. A. T. McManus, Chief, Microbiology Branch, U.S. Army Institute of Surgical Research, Fort Sam Houston, Tex.). The seventh group served as non-infected and non-treated control.

In group one, the burned and seeded skin was treated with 0.5 ml of 100 $\mu$M of LSB-37 in PBS. The LSB-PBS was sprayed onto the burned area, and gently rubbed into the clipped hair by a gloved finger. These rats were also inoculated intramuscularly in the thigh muscles of both right and left legs (alternating) with a dose of LSB-37 in PBS equal to 5.0 mg of peptide per pound of body weight. The intramuscular injections were begun 20 hours post burn infection, and were repeated every six hours for three days.

Group two rats received 0.5 to 1.0 ml of PBS sprayed on and rubbed into the burned areas. The burned and seeded skin of group three rats was treated with 1% silver sulfadizaine cream (Tine SSD S-901842- Exp. March,89). The cream was digitally applied to the burn at a thickness of approximately 1.0 mm. The burned and seeded skin of group four rats was treated topically only with LSB-37 beginning at nine hours post burn-infection. All treatments were begun at nine hours post burn-infection, and repeated every six hours for three days.

Of the 35 test rats, five did not recover from the general anesthesia. Three additional rats in the control group (burned, but not infected nor treated) died. These rats were replaced with three additional rats which were then maintained in a separate cage for the duration of the experiment. One animal in group four and one in group six did not recover from the anesthesia. Several rats were moribund, or had been traumatized by cannibalism and were euthanatized by an overdose of ether anesthetic. The following table illustrates the number of surviving animals.

TABLE XI

| TITLE | |
|---|---|
| Burned, not infected | 5 |
| Topical PBS | 0 |
| Topical Silver Sulfadiazine | 5 |
| Topical LSB-37 at 9 hours | 1 |
| Topical LSB-37 at 20 hours | 1 |
| I.M. LSB-37 at 20 hours | 1 |
| Topical at 9; I.M. at 20 hours | 0 |

Figure 8A:
FIGS. 8A and 8B show photographs of rats burned and treated with lytic peptides to enhance wound healing.
Figure 8B:

The high mortality rate due to cannibalism, failure to recover from the anesthesia, and secondary infection by gram positive bacteria make it difficult to draw conclusions from the numbers generated. However, the dramatic recovery of the wound in the live animals treated with the lytic peptide LSB-37 suggests a profound effect of this peptide on would healing. Photographs shown in FIG. 8 of surviving animals clearly show the animals treated either topically or by injection with LSB-37 have vastly accelerated regeneration of the tissue over the wound, with less scarring, and accelerated hair growth.

What is claimed is:

1. A method of killing microbes comprising: contacting said microbes with an effective dose of a therapeutic composition comprising a peptide of 18 to about 40 amino acids, and a carrier, wherein the peptide comprises:

(a) a portion that is an α-helical conformation comprising approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino acids are of the sequence: lysine-arginine-lysine-arginine.

2. A method of treatment for microbial infection in animals comprising: admininstering to the animals an effective dose of a therapeutic composition comprising a peptide of 18 to about 40 amino acids, and a carrier, wherein the peptide comprises:
(a) a portion that is an α-helical conformation comprising approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino acids are of the sequence: lysine-arginine-lysine-arginine.

3. A method for the treatment of cancer in an animal comprising: administering to an animal an effective dose of a therapeutically active composition comprising a peptide of 18 to about 40 amino acids, and a carrier, wherein the peptide comprises:
(a) a portion that is an α-helical conformation comprising approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino acids are of the sequence: lysine-arginine-lysine-arginine.

4. A method for the proliferation of cell growth comprising: contacting cells with an effective dose of a therapeutic composition comprising a peptide of 18 to about 40 amino acids, and a carrier, wherein the peptide comprises:
(a) a portion that is an α-helical conformation comprising approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino acids are of the sequence: lysine-arginine-lysine-arginine.

5. A method for the healing of wounds comprising: administering to a wound an effective dose of a therapeutic composition comprising a peptide of 18 to about 40 amino acids, and a carrier, wherein the peptide comprises:
(a) a portion that is an α-helical conformation comprising on approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino adds are of the sequence: lysine-arginine-lysine-arginine.

6. A method to facilitate the action of a therapeutic agent, the method comprising: administering a composition comprising the therapeutic agent and an effective dose of a peptide of 18 to about 40 amino acids, and a carrier, wherein the peptide comprises:
(a) a portion that is an α-helical conformation comprising approximately 15 to 40 amino acids;
(b) one or more sets of 18 sequential amino acids, each amino acid spaced about 20 degrees apart about the axis of the helix, exhibiting approximately 60–100% aligned amphipathy; and
(c) four or more positively charged amino acids; wherein:
the amino acid at position 19 is not glutamate or aspartate;
the amino acid at position 23 or 24 is not proline; and
no four consecutive amino acids are of the sequence: lysine-arginine-lysine-arginine.

7. The method of claim 1, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis4, Anubis-5, Anubis-8, Vishnu-1, Vishnu-2, Vishnu-3, or Vishnu-8.

8. The method of claim 2, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis-4, Anubis-5, Anubis-8, Vishnu-1, Vishnu-2, Vishnu-3, or Vishnu-8.

9. The method of claim 3, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis-4, Anubis-5, Anubis-8, Vishnu-1 , Vishnu-2, Vishnu-3, or Vishnu-8.

10. The method of claim 4, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis-4, Anubis-5, Anubis-8, Vishnu-1, Vishnu-2, Vishnu-3, or Vishnu-8.

11. The method of claim 5, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis-4, Anubis-5, Anubis-8, Vishnu-1, Vishnu-2, Vishnu-3, or Vishnu-8.

12. The method of claim 6, wherein the peptide is SB-37*, LSB-37, SB-37, Shiva-1, Shiva-10, Shiva-11, Shiva-12, β-fibrin signal, Manitou-1, Manitou-2, Hecate-1, Hecate-2, Hecate-3, Anubis-1, Anubis-2, Anubis-3, Anubis-4, Anubis-5, Anubis-8, Vishnu-1, Vishnu-2, Vishnu-3, or Vishnu-8.

13. The method of claim 1, wherein the pathogenic microorganisms are bacteria.

14. The method of claim 1, wherein the pathogenic microorganisms are gram positive bacteria or gram negative bacteria.

15. The method of claim 2, wherein the infection is a bacterial infection.

16. The method of claim 2, wherein the infection is an extracellular infection.

17. The method of claim 2, wherein the infection is an intracellular infection.

18. The method of claim 2, wherein the administering is performed by topical application, injection, or infusion.

19. The method of claim 3, wherein the administering is performed by topical application, injection, or infusion.

20. The method of claim 4, wherein the cells are white blood cells, lymphocytes, or fibroblasts.

21. The method of claim 4, wherein the contacting step is performed in vitro.

22. The method of claim 4, wherein the contacting step is performed in vivo.

23. The method of claim 5, wherein the administering step is performed by topical application, injection, or infusion.

24. The method of claim 6, wherein the therapeutic agent is an antiinfective agent, a cancer therapy agent, a vaccine, an antifungal agent, or an antibiotic.

* * * * *